United States Patent
Cowen et al.

(10) Patent No.: US 7,179,902 B2
(45) Date of Patent: Feb. 20, 2007

(54) USE OF REGULATORY SEQUENCES IN TRANSGENIC PLANTS

(75) Inventors: Neil M. Cowen, Carlsbad, CA (US); Katherine Armstrong, Zionsville, IN (US); Kelley A. Smith, Lebanon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 493 days.

(21) Appl. No.: 10/603,524

(22) Filed: Jun. 25, 2003

(65) Prior Publication Data

US 2004/0158887 A1 Aug. 12, 2004

Related U.S. Application Data

(60) Provisional application No. 60/392,571, filed on Jun. 27, 2002.

(51) Int. Cl.
*A01H 1/00* (2006.01)
*C07H 21/04* (2006.01)
*C12N 5/14* (2006.01)
*C12N 15/09* (2006.01)

(52) U.S. Cl. .................. 536/24.1; 435/6; 435/468; 435/419; 435/253.3; 435/320.1; 435/536; 536/23.1; 800/278; 800/295

(58) Field of Classification Search ................ None
See application file for complete search history.

(56) References Cited

U.S. PATENT DOCUMENTS 5,362,865 A 11/1994 Austin .................. 536/24.1

OTHER PUBLICATIONS

Paek et al. (NCBI, GenBank, Sequence Accession No. L35913, Published Aug. 26, 1994).*
Ingelbrecht et al. (The Plant Cell, 1:671-680, 1989).*
de Vetten, N.C., et al. "Two Genes Encoding GF14 (14-3-3) Proteins in *Zea mays*", Plant Physiol. (1994) 106: 1593-1604.
Brendel, V., et al., "Intron Recognition in Plants" American Society of Plant Physiologists (1998).
Johnson, M.A., et al. "Determinants of mRNA Stability in Plants" American Society of Plant Physiologists (1998).
Marcotte, Jr. W.R., et al. "Developmental Regulation of Translation and mRNA Stability" American Society of Plant Physiologists (1998).
Schuler, M.A. "Plant pre-mRNA Splicing" American Society of Plant Physiologists (1998).
Paek, N.C., et al. "Inhibition of Germination Gene Expression by *Viviparous-1* and ABA during Maize Kernel Development" Molecules and Cells, vol. 8, No. 3, pp. 336-342 (1998).

* cited by examiner

*Primary Examiner*—Phuong T Bui
*Assistant Examiner*—Vinod Kumar
(74) *Attorney, Agent, or Firm*—Ronald Maciak (57) ABSTRACT

The present invention provides DNA sequences that function as 3' untranslated regions (3'UTR) in plants. The 3'UTR's stabilize associated recombinant transcripts such that expression is improved. The invention further provides plant expression cassettes and recombinant plant that comprise a claimed 3'UTR.

4 Claims, 1 Drawing Sheet

Figure 1

SEQUENCE LISTING

```
<160> NUMBER OF SEQ ID NOS: 4

<210> SEQ ID NO 1
<211> LENGTH: 332
<212> TYPE: DNA
<213> ORGANISM: Zea mays
<220> FEATURE:
<221> NAME/KEY: misc_feature
<222> LOCATION: (65)..(65)
<223> OTHER INFORMATION: N may be A, T, C, or G
<220> FEATURE:
<221> NAME/KEY: misc_feature
<222> LOCATION: (159)..(159)
<223> OTHER INFORMATION: N may be A, T, C, or G
<220> FEATURE:
<221> NAME/KEY: misc_feature
<222> LOCATION: (269)..(269)
<223> OTHER INFORMATION: N may be A, T, C, or G

<400> SEQUENCE: 1
ggtcgcagcg tgtgcgtgtc cgtcgtacgt tctggccggc cgggccttgg gcgcgcgatc      60 agaacgttg cgttggcgtg tgtgtgcttc tggtttgctt taattttacc aagtttgttt     120
caaggtggat cgcgtggtca aggcccgtgt gctttaaana cccaccggca ctggcagtga    180
gtgttgctgc ttgtgtaggc tttggtacgt atgggcttta tttgcttctg gatgttgtgt    240
actacttggg tttgttgaat tattatganc agttgcgtat tgtaattcag ctgggctacc    300
tggacattgt tatgtattaa taaatgcttt gc                                   332
```

<210> SEQ ID NO 2
<211> LENGTH: 291
<212> TYPE: DNA
<213> ORGANISM: Zea mays

<400> SEQUENCE: 2

| | | | | |
|---|---|---|---|---|
| agccggcttt | atgtgcgtag | aaactagtag | ctagtgtttg | ctgctgtcga | atgacactat | 60 |
| gcaatgtgat | ctggaacctg | gtttcttggg | tgcgacgcta | gttatgactg | tcgtcagtaa | 120 |
| aatttggggg | ctccccgtat | gagatgctgc | cgggcaaggc | ctcggtgtcc | cacctcgttt | 180 |
| gtggcggggg | gcgctggagc | ccggtctggt | tgggttggga | agccctttaa | actgttgtca | 240 |
| cttgcatttt | accttttcca | tcgctgttta | ttgtgagtgg | tcctatatca | a | 291 |

<210> SEQ ID NO 3
<211> LENGTH: 1436
<212> TYPE: DNA
<213> ORGANISM: Zea mays

<400> SEQUENCE: 3

| | | | | | | |
|---|---|---|---|---|---|---|
| aagcttgccg | agtgccatcc | ttggacactc | gataaagtat | attttatttt | ttttattttg | 60 |
| ccaaccaaac | tttttgtggt | atgttcctac | actatgtaga | tctacatgta | ccattttggc | 120 |
| acaattacaa | aaatgttttc | tataactatt | agatttagtt | cgtttatttg | aatttcttcg | 180 |
| gaaaattcac | atatgaactg | caagtcactc | gaaacatgaa | aaaccgtgca | tgcaaaataa | 240 |
| atgatatgca | tgttatctag | cacaagttac | gaccgatttc | agaagcagac | cagaatcttc | 300 |
| aagcaccatg | ctcactaaac | atgaccgtga | acttgttatc | cagttgttta | aaaattgtat | 360 |
| aaaacacaaa | taaagtcaga | aattaatgaa | acttgtccac | atgtcatgat | atcatatata | 420 |
| gaggttgtga | taaaaatttg | atattgtttc | ggtaaagttg | tgacgtacta | tgtgtagaaa | 480 |
| cctaagtgac | ctacacataa | aatcatagag | tttcaatgta | gttcactcga | caaagacttt | 540 |
| gtcaagtgtc | cgataaaaag | tattcagcaa | agaagccgtt | gtcgatttac | tgttcgtcga | 600 |
| gatctctttg | ccgagtgtca | cactaggcaa | agtctttacg | gagttgtttt | tcaggctttg | 660 |
| acactcggca | aagcgctcga | ttccagtagt | ggacagtaat | ttgcatcaaa | aatagccgag | 720 |
| agatttaggc | cccgtttcaa | tctcacggga | taaagtttag | cttcctgcta | aactttagct | 780 |
| atatgaattg | aagtgctaaa | gtttagtttc | aattaccacc | attagctctc | ctgtttagat | 840 |
| tacaaatggc | taaagtagc | taaaaaatag | ctgctaaagt | ttatctcgcg | agattgaaac | 900 |
| agggccttaa | aatgagtcaa | ctaatagacc | aactaattat | tagctattag | tcgttagctt | 960 |
| ctttaatcta | agctaaaacc | aactaatagc | ttatttgttg | aattacaatt | agctcaacgg | 1020 |
| aattctctgt | tttttctata | aaaaggaa | actgcccctc | atttacagca | aactgtccgc | 1080 |
| tgcctgtcgt | ccagatacaa | tgaacgtacc | tagtaggaac | tcttttacac | gctcggtcgc | 1140 |
| tcgccgcgga | tcggagtccc | aggaacacga | caccactgtg | gaacacgaca | aagtctgctc | 1200 |
| agaggcggcc | acaccctggc | gtgcaccgag | ccggagcccg | gataagcacg | gtaaggagag | 1260 |
| tacggcggga | cgtggcgacc | cgtgtgtctg | ctgccacgca | gccttcctcc | acgctagccg | 1320 |
| cgcggccgcg | ccacgtacca | gggcccggcg | ctggtataaa | tgcgcgccac | ctccgcttta | 1380 |
| gttctgcata | cagccaaccc | aacacacacc | cgagcatatc | acagtgacac | tacacc | 1436 |

<210> SEQ ID NO 4
<211> LENGTH: 362
<212> TYPE: DNA
<213> ORGANISM: Zea mays

```
<400> SEQUENCE: 4
gggcactgaa gtcgcttgat gtgctgaatt gtttgtgatg ttggtggcgt attttgttta        60
aataagtaag catggctgtg attttatcat atgatcgatc tttggggttt tatttaacac       120
attgtaaaat gtgtatctat taataactca atgtataaga tgtgttcatt cttcggttgc       180
catagatctg cttatttgac ctgtgatgtt ttgactccaa aaaccaaaat cacaactcaa       240
taaactcatg gaatatgtcc acctgtttct tgaagagttc atctaccatt ccagttggca       300
tttatcagtg ttgcagcggc gctgtgcttt gtaacataac aattgttcac ggcatatatc       360
ca                                                                     362
```

USE OF REGULATORY SEQUENCES IN TRANSGENIC PLANTS

RELATED APPLICATIONS

This application claims the benefit of U.S. Provisional Application No. 60/392,571, filed Jun. 27, 2002.

FIELD OF THE INVENTION

This invention relates to genetic engineering of plants. More particularly, the invention provides DNA sequences and constructs that are useful to stabilize recombinant transcripts in plants.

BACKGROUND OF THE INVENTION

Through the use of recombinant DNA technology and genetic engineering, it has become possible to introduce foreign DNA sequences into plant cells to allow for the expression of proteins of interest. However, obtaining desired levels of expression remains a challenge. To express agronomically important transgenes in crops at desired levels requires the ability to control the regulatory mechanisms governing expression in plants, and this requires suitable regulatory sequences that can function with the desired transgenes.

A given project may require use of several different expression elements, for example one set to drive a selectable marker or reporter gene and another to drive the gene of interest. The selectable marker may not require the same expression level or pattern as that required for the gene of interest. Depending upon the particular project, there may be a need for constitutive expression, which directs transcription in most or all tissues at all time, or there may be a need for tissue specific expression.

Cells use a number of regulatory mechanisms to control which genes are expressed and the level at which they are expressed. Regulation can be transcriptional or post-transcriptional and can include, for example, mechanisms to enhance, limit, or prevent transcription of the DNA, as well as mechanisms that limit the life span of the mRNA after it is produced. The DNA sequences involved in these regulatory processes can be located upstream, downstream or even internally to the structural DNA sequences encoding the protein product of a gene.

Initiation of transcription of a gene is regulated by the promoter sequence located upstream (5') of the coding sequence. Eukaryotic promoters generally contain a sequence with homology to the consensus TATA box about 10–35 base pairs (bp) upstream of the transcription start (CAP) site. Most maize genes have a TATA box about 29 to 34 base pairs upstream of the CAP site. In most instances the TATA box is required for accurate transcription initiation. Further upstream, often between −80 and −100, there can be a promoter element with homology to the consensus sequence CCAAT. This sequence is not well conserved in many species including maize. However, genes having this sequence appear to be efficiently expressed. In plants, the CCAAT "box" is sometimes replaced by the AGGA "box". Other sequences conferring tissue specificity, response to environmental signals or maximum efficiency of transcription may be found interspersed with these promoter elements or found further in the 5' direction from the CAP site. Such sequences are often found within 400 bp of the CAP site, but may extend as far as 1000 bp or more.

Promoters can be classified into two general categories. "Constitutive" promoters are expressed in most tissues most of the time. Expression from a constitutive promoter is more or less at a steady state level throughout development. Genes encoding proteins with house-keeping functions are often driven by constitutive promoters. Examples of constitutively expressed genes in maize include actin and ubiquitin. Wilmink et al. (1995), *Plant Molecular Biology* 28:949–955. "Regulated" promoters are typically expressed in only certain tissue types (tissue specific promoters) or at certain times during development (temporal promoters). Examples of tissue specific genes in maize include the zeins which are abundant storage proteins found only in the endosperm of seed. Kriz, A. L. et al. (1987), *Molecular and General Genetics* 207: 90–98. Many genes in maize are regulated by promoters that are both tissue specific and temporal.

It has been demonstrated that promoters can be used to control expression of foreign gene sequences in transgenic plants in a manner similar to the expression pattern of the gene from which the promoter was originally derived. The most thoroughly characterized promoter tested with recombinant genes in plants has been the 35S promoter from the Cauliflower Mosaic Virus (CaMV) and its derivatives. U.S. Pat. No. 5,352,065; Wilmink, et al. (1995); Datla, R. S. S. et al. (1993), *Plant Science* 94:139–149. Elegant studies conducted by Benfey, et al. (1984) reveal that the CaMV 35S promoter is modular in nature with regards to binding to transcription activators. U.S. Pat. No. 5,097,025; Benfey P. N., L. Ren and N.-H. Chua. (1989), *EMBO Journal* 8:2195–2202; Benfey, P. N., and Nam-Hai Chua. (1990), *Science* 250:959–966. Two independent domains result in the transcriptional activation that has been described by many as constitutive. The 35S promoter is very efficiently expressed in most dicots and is moderately expressed in monocots. The addition of enhancer elements to this promoter has increased expression levels in maize and other monocots. Constitutive promoters of monocot origin have not been as thoroughly studied to date and include the polyubiquitin-1 promoter and the rice actin-1 promoter. Wilmink, et al. (1995). In addition, a recombinant promoter, Emu, has been constructed and shown to drive expression in monocots in a constitutive manner. Wilmink, et al. (1995).

DNA sequences called enhancer sequences have been identified which have been shown to enhance gene expression when placed proximal to the promoter. Such sequences have been identified from viral, bacterial, mammalian, and plant gene sources. An example of a well characterized enhancer sequence is the ocs sequence from the octopine synthase gene in *Agrobacterium tumefaciens*. This short (40 bp) sequence has been shown to increase gene expression in both dicots and monocots, including maize, by significant levels. Tandem repeats of this enhancer have been shown to increase expression of the GUS gene eight-fold in maize. It remains unclear how these enhancer sequences function. Presumably enhancers bind activator proteins and thereby facilitate the binding of RNA polymerase II to the TATA box. Grunstein, M. (1992), *Scientific American*, October 68–74. PCT Published Application WO95/14098 describes testing of various multiple combinations of the ocs enhancer and the mas (mannopine synthase) enhancer which resulted in several hundred fold increase in gene expression of the GUS gene in transgenic tobacco callus.

The 5' untranslated leader sequence of mRNA, introns, and the 3' untranslated region of mRNA affect expression by their effect on post-transcription events, for example by facilitating translation or stabilizing mRNA.

Expression of heterologous plant genes has also been improved by optimization of the non-translated leader sequence, i.e. the 5' end of the mRNA extending from the 5' CAP site to the AUG translation initiation codon of the mRNA. The leader plays a critical role in translation initiation and in regulation of gene expression. For most eukaryotic mRNAs, translation initiates with the binding of the CAP binding protein to the mRNA CAP. This is then followed by the binding of several other translation factors, as well as the 43S ribosome pre-initiation complex. This complex travels down the mRNA molecule scanning for an AUG initiation codon in an appropriate sequence context. Once located, a 60S ribosomal subunit binds the complex to create the complete 80S ribosomal complex that initiates mRNA translation and protein synthesis. Pain (1986), *Biochem. J.*, 235:625–637; Kozak (1986), *Cell* 44:283–292. Optimization of the leader sequence for binding to the ribosome complex has been shown to increase gene expression as a direct result of improved translation initiation efficiency. Significant increases in gene expression have been produced by addition of leader sequences from plant viruses or heat shock genes. Raju, S. S. D. et al (1993), *Plant Science* 94: 139–149.

The 3' end of the mRNA can also have a large effect on expression, and is believed to interact with the 5' CAP. Sullivan, M. L and P. Green (1993), *Plant Molecular Biology* 23: 1091–1104. The 3'untranslated region (3'UTR) has been shown to have a significant role in gene expression of several maize genes. Specifically, a 200 base pair, 3'UTR has been shown to be responsible for suppression of light induction of the maize small m3 subunit of the ribulose-1, 5-biphosphate carboxylase gene (rbc/m3) in mesophyll cells. Viret, J.-F. et al. (1994), *Proc. Nat Acad. Sci.* 91:8577–8581. Some 3'UTRs have been shown to contain elements that appear to be involved in instability of the transcript. Sullivan, et al. (1993). The 3'UTRs of most eukaryotic genes contain consensus sequences for polyadenylation. In plants, especially maize, this sequence is not very well conserved. The 3' UTR, including a polyadenylation signal, derived from a nopaline synthase gene (3' nos) is frequently used in plant genetic engineering. Few examples of heterologous 3'UTR testing in maize have been published.

Important aspects of the present invention are based on the discovery that a 3' UTR derived from a constitutive maize lipase gene, viviparous 1 (Vp1) described by Paek, et al. (1998) *Mol. Cells*, 8(3), 336–342, and a 3' UTR of the maize general regulatory factor-1 (GRF1) gene described by de Vetten et al. (1994), *Plant Physiol*, 106(4), 1593–604, are exceptionally useful for stabilizing recombinant transgene mRNAs in plants.

SUMMARY OF THE INVENTION

The invention provides isolated non-coding DNA molecules that are used in the claimed method for improving the expression of transgenes in plants. These DNA sequences are situated 3' to an open reading frame in recombinant constructs and function to stabilize recombinant gene transcripts in plants. The present invention further provides recombinant gene expression cassettes useful for effecting expression of a transgene of interest in transformed plants. These cassettes comprise the following elements that are operably linked from 5' to 3'.

1) a gene promoter sequence that expresses in plants;
2) an untranslated leader sequence;
3) a foreign coding sequence of interest;
4) a 3'UTR selected from the group consisting of SEQ ID NO: 1 and SEQ ID NO:2.

In another of its aspects, the invention provides a transformed plant comprising at least one plant cell that contains a DNA construct of the invention. The plant may be a monocot or dicot. Preferred plants are maize, rice, cotton and tobacco. In another of its aspects, the invention provides seed or grain that contains a DNA construct of the invention.

DETAILED DESCRIPTION OF THE INVENTION

In one of its aspects, the present invention relates to 3'UTR sequences derived from maize genes that are able to stabilize mRNA sequences transcribed from transgenes thereby improving expression of recombinant genes in plants. One such group of 3'UTRs were derived from the Vp1 maize lipase gene and is shown in SEQ ID NO:1.

SEQ ID NO: 1 is 332 base pairs in length and contains three variable nucleotides (positions 59, 145, and 245), any of which may vary independently to any one of A,T,C, or G. In a preferred embodiment all three variable nucleotides are G.

The invention further provides an isolated DNA molecule derived from the maize GRF1 gene that is 291 base pairs in length and is shown in SEQ ID NO:2.

These stabilizing 3'UTR sequences provide their function when located immediately 3' to an open reading frame of a transgene of interest such that when the transgene is transcribed the resulting mRNA contains the 3'UTR immediately downstream of the coding region.

In accordance with the foregoing unexpected and significant findings, the invention provides plant expression cassettes that are useful for improving the expression of transgenes in plants. These cassettes comprise the following elements that are operably linked from 5' to 3'.

1) a plant gene promoter sequence that naturally expresses in plants;
2) an untranslated leader sequence;
3) a foreign coding sequence of interest;
4) a 3'UTR selected from the group consisting of SEQ ID NO: 1 and SEQ ID NO:2.

Promoters useful in this embodiment are any known promoters that are functional in a plant. Many such promoters are well known to the ordinarily skilled artisan. Such promoters include promoters normally associated with other genes, and/or promoters isolated from any bacterial, viral, eukaryotic, or plant cell. It may be advantageous to employ a promoter that effectively directs the expression of the foreign coding sequence in the cell or tissue type chosen for expression. The use of promoter and cell type combinations for protein expression is generally known to those of skill in the art of molecular biology, for example, see Sambrook et al., In: Molecular Cloning: A Laboratory Manual, Cold Spring Harbor Laboratory, Cold Spring Harbor, N.Y., 1989. The promoters employed may be constitutive, or inducible, and can be used under the appropriate conditions to direct high level expression of the introduced DNA segment, such as is advantageous in the large-scale production of recombinant proteins or peptides. The promoter may be in the form of a promoter that is naturally associated with the foreign coding sequence of interest, as may be obtained by isolating the 5' non-coding sequences located upstream of the coding segment.

A preferred group of promoters is the ubiquitin family of promoters described in U.S. Pat. No. 5,510,474, herein incorporated by reference in its entirety; the cassava vein mosaic virus promoters described in U.S. Pat. No. 7,053,205 B1, herein incorporated by reference in its entirety; the phaseolin promoters described in U.S. Pat. No. 5,591,605, herein incorporated by reference in its entirety; rice actin promoters described in U.S. Pat. No. 5,641,876, herein incorporated by reference in its entirety; the per5 promoter described in WO 98/56921, herein incorporated by reference in its entirety; and the gamma zein promoters described in WO 00/12681. A more highly preferred group is the ubiquitin promoters and the rice actin promoters.

The untranslated leader sequence, 5'UTR, can be derived from any suitable source and may be specifically modified to increase the translation of the mRNA. The 5' non-translated region may be obtained from the promoter selected to express the gene, the native leader sequence of the gene or coding region to be expressed, viral RNAs, suitable eukaryotic genes, or may be a synthetic sequence. The untranslated leader used with the present invention is not critical. The untranslated leader will typically be one that is naturally associated with the promoter. The untranslated leader may be one that has been modified to include an intron. It may also be a heterologous sequence, such as one provided by U.S. Pat. No. 5,362,865, herein incorporated by reference in its entirety.

The foreign coding sequence of interest may be any gene that it is desired to express in plants. Particularly useful genes are those that confer tolerance to herbicides, insects, or viruses, and genes that encode medicinal proteins such as antibodies, protein hormones, and cytokines as well as genes that provide improved nutritional value or processing characteristics of the plant. Examples of suitable agronomically useful genes include the insecticidal gene from *Bacillus thuringiensis* for conferring insect resistance and the 5'-enolpyruvyl-3'-phosphoshikimate synthase (EPSPS) gene and any variant thereof for conferring tolerance to glyphosate herbicides. As is readily understood by those skilled in the art, any agronomically and medicinally important genes conferring a desired input or output trait can be used.

Construction of gene cassettes utilizing the 3'UTR herein disclosed is readily accomplished utilizing well known methods, such as those disclosed in Sambrook et al. (1989); and Ausubel et al. (1987) *Current Protocols in Molecular Biology*, John Wiley and Sons, New York, N.Y.

The present invention also includes DNA sequences having substantial sequence homology with the specifically disclosed regulatory sequences, such that they are able to have the disclosed effect on expression. As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

In most cases, sequences having 95% homology to the sequences specifically disclosed herein will function as equivalents, and in many cases considerably less homology, for example 75% or 80%, will be acceptable. Locating the parts of these sequences that are not critical may be time consuming, but is routine and well within the skill in the art. Exemplary techniques for modifying oligonucleotide sequences include using polynucleotide-mediated, site-directed mutagenesis. See Zoller et al. (1984); Higuchi et al. (1988); Ho et al. (1989); Horton et al. (1989); and *PCR Technology: Principles and Applications for DNA Amplification*, (ed.) Erlich (1989).

In one embodiment, an expression cassette, pMYC3212, (FIG. 1) of this invention, comprises, in the 5' to 3' direction, the maize globin promoter shown in SEQ ID NO: 3 (Belanger, et al., *Genetics*, 129(3), 863–72, 1991), in reading frame with the myo-inositol-O-methyl transferase (IMT) gene from *Mesembryanthemum crystallinum* (U.S. Pat. No. 5,563,324, herein incorporated by reference in its entirety) regulated by the per5 3'UTR shown in SEQ ID NO:4. The vector incorporates the PAT selectable marker gene (U.S. Pat. Nos. 5,879,903; 5,637,489; 5,276,268; and 5,273,894 herein incorporated by reference in their entirety) driven by the maize ubiquitin-1 promoter (U.S. Pat. Nos. 5,510,474; 5,614,399; 6,020,190; 6,054,574 herein incorporated by reference in their entirety) and terminated with a 3'UTR of SEQ ID NO:1.

Figure 1:
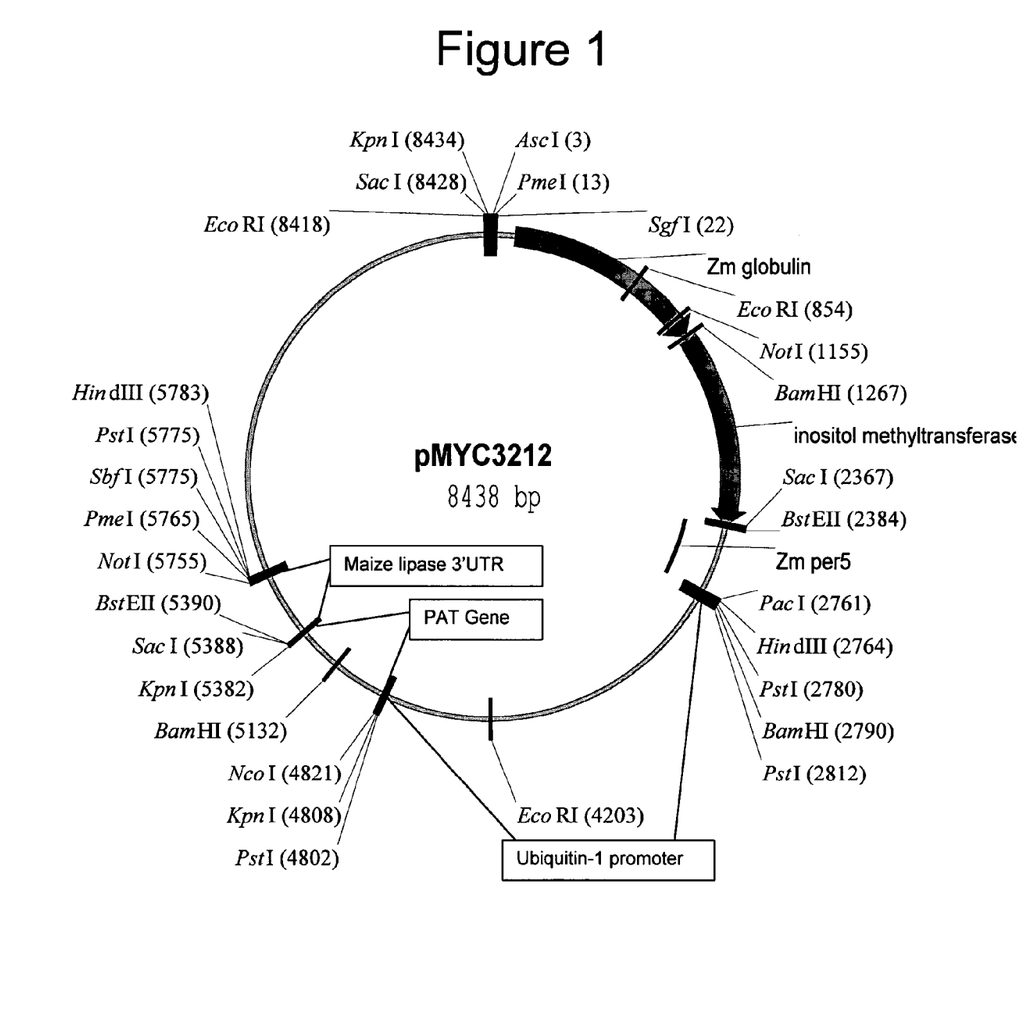
FIG. 1 is a depiction of the pMYC3212 expression vector for the myo-inositol-O-methyl transferase (IMT) gene from *Mesembryanthemum crystallinum* driven by the zea maize globin promoter. The vector incorporates the PAT selectable marker driven by the maize ubiquitin-1 promoter and terminated with a 3'UTR of SEQ ID NO:1.

The IMT gene product has been shown to convert myo-inositol to pinitol in transgenic plants. The expression cassette may be used in a variety of ways, including for example, insertion into a plant cell for the expression of the nucleic acid sequence of interest.

A promoter DNA sequence is said to be "operably linked" to a coding DNA sequence if the two are situated such that the promoter DNA sequence influences the transcription of the coding DNA sequence. For example, if the coding DNA sequence codes for the production of a protein, the promoter DNA sequence would be operably linked to the coding DNA sequence if the promoter DNA sequence affects the expression of the protein product from the coding DNA sequence. For example, in a DNA sequence comprising a promoter DNA sequence physically attached to a coding DNA sequence in the same chimeric construct, the two sequences are likely to be operably linked.

The DNA sequence associated with the regulatory or promoter DNA sequence may be heterologous or homologous, that is, the inserted genes may be from a plant of a different species than the recipient plant. In either case, the DNA sequences, vectors and plants of the present invention are useful for directing transcription of the associated DNA sequence so that the mRNA transcribed or the protein encoded by the associated DNA sequence is efficiently expressed.

Promoters are positioned 5' (upstream) to the genes that they control. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art and demonstrated herein with multiple copies of regulatory elements, some variation in this distance can occur.

Any plant-expressible foreign coding sequence can be used in these constructions. A foreign coding is the sequence of a gene comprising a DNA segment encoding a protein, polypeptide, antisense RNA or ribozyme or a portion thereof. Notwithstanding the adjective "foreign" the term "foreign coding sequence" can refer to a coding sequence naturally found within the cell, but artificially introduced. Foreign coding sequence may also encode a protein not normally found in the plant cell into which the gene is introduced, in which case it may be referred to as a heterologous coding sequence.

The foreign coding sequence may code, for example, for proteins known to inhibit insects or plant pathogens such as fungi, bacteria and nematodes. These proteins include, but are not limited to, plant non-specific lipid acyl hydrolases, especially patatin; midgut-effective plant cystatins, especially potato papain inhibitor; magainins, Zasloff (1987), *PNAS USA*, 84:5449–5453; cecropins, Hultmark et al. (1982), *EUR. J. Biochem.*, 127:207–217; attacins, Hultmark et al. (1983), *EMBO J.*, 2:571–576; melittin; gramicidin S, Katsu et al. (1988), *Biochim. Biophys. Acta*, 939:57–63; sodium channel proteins and synthetic fragments, Oiki et al. (1988), *PNAS USA*, 85:2393–2397: the alpha toxin of *Staphylococcus aureus*, Tobkes et al. (1985), *Biochem.* 24:1915–1920; apolipoproteins and fragments thereof, Knott et al. (1985), *Science*, 230:37; alamethicin and a variety of synthetic amphipathic peptides, Kaiser et al. (1987), *Ann. Rev Biophys. Biophys. Chem.*, 16:561–581); lectins, Lis et al. (1986), *Ann. Rev. Biochem.*, 55:35–68 and Van Parijis et al. (1991), *Planta*, 183:258; pathogenesis-related proteins, Linthorst (1991), *Critical Rev. Plant Sci.*, 10:123–150; osmotins and permatins, Vigers et al. (1992), *Plant Sci.*, 83:155; chitinases; glucanases, Lewah et al. (1991), *J. Biol. Chem.*, 266:1564–1573; thionins, Bohlmann and Apel (1991), *Annu. Rev. Plant Physiol Plant Mol. Biol.*, 42:227–240; protease inhibitors, Ryan (1990), *Annu Rev. Phytopathol.*, 28:425; plant anti-microbial peptides, Cammue et al. (1992), *J. Biol. Chem*, 267:2228–2233; and polypeptides from *Bacillus thuringiensis*, which are postulated to generate small pores in the insect gut cell membrane, nowles et al. (1987), *Biochim. Biophys. Acta* 924:509–518 and Hofte and Whitely (1989), *Microbiol. Rev.*, 53:242–255.

The foreign coding sequence may also encode multimeric, and optionally glycosylated proteins as described in U.S. Pat. No. 5,202,422, herein incorporated in its entirety by reference, antibody genes as described in U.S. Pat. No. 5,959,177, herein incorporated in its entirety by reference, and medicinally useful antigens as described in U.S. Pat. No. 5,679,880, herein incorporated in its entirety by reference.

The coding sequence may be derived in whole or in part from a bacterial genome or episome, eukaryotic genomic, mitochondrial or plastid DNA, cDNA, viral DNA, or chemically synthesized DNA. It is possible that a coding sequence may contain one or more modifications in coding region which may affect the biological activity or the chemical structure of the expression product, the rate of expression, or the manner of expression control. Such modifications include, but are not limited to, mutations, insertions, deletions, rearrangements and substitutions of one or more nucleotides. The coding sequence may constitute an uninterrupted coding sequence or it may include one or more introns, bounded by the appropriate plant-functional splice junctions. The coding sequence may be a composite of segments derived from a plurality of sources, naturally occurring or synthetic. The structural gene may also encode a fusion protein, so long as the experimental manipulations maintain functionality in the joining of the coding sequences.

The use of a signal sequence to secrete or sequester in a selected organelle allows the protein to be in a metabolically inert location until released in the gut environment of an insect pathogen. Moreover, some proteins are accumulated to higher levels in transgenic plants when they are secreted from the cells, rather than stored in the cytosol. Hiatt, et al. (1989), *Nature*, 342:76–78.

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure; in some cases hybrid constructions are preferred, combining promoter elements upstream of the tissue preferential promoter TATA and CAAT box to a minimal 35S derived promoter consisting of the 35S TATA and CAAT box. Finally, the vectors should desirably have a marker gene that is capable of providing a phenotypical property which allows for identification of host cells containing the vector, and an intron in the 5' untranslated region, e.g., intron 1 from the maize alcohol dehydrogenase gene that enhances the steady state levels of mRNA of the marker gene.

The activity of the foreign coding sequence inserted into plant cells is dependent upon the influence of endogenous plant DNA adjacent the insert. Generally, the insertion of heterologous genes appears to be random using any transformation technique; however, technology currently exists for producing plants with site specific recombination of DNA into plant cells (see WO 91/09957). The particular methods used to transform such plant cells are not critical to this invention, nor are subsequent steps, such as regeneration of such plant cells, as necessary. Any method or combination of methods resulting in the expression of the desired sequence or sequences under the control of the promoter is acceptable.

There are many methods well know in the art for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA, for example, by PEG-mediated transformation of protoplasts (Omirulleh et al., *Plant Molecular Biology*, 21:415–428, 1993.), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introducing f DNA into cells is well-known to those of skill in the art. Four basic methods for delivering foreign DNA into plant cells have been described. Chemical methods (Graham and van der Eb, *Virology*, 54(02):536–539, 1973; Zatloukal, Wagner, Cotten, Phillips, Plank, Steinlein, Curiel, Birnstiel, *Ann. N.Y. Acad. Sci.*, 660:136–153, 1992); Physical methods including microinjection (Capecchi, *Cell*, 22(2):479–488, 1980), electroporation (Wong and Neumann, *Biochim. Biophys. Res. Commun.* 107(2):584–587, 1982; Fromm, Taylor, Walbot, *Proc. Natl. Acad. Sci. USA*, 82(17):5824–5828,1985; U.S. Pat. No. 5,384,253) and the gene gun (Johnston and Tang, *Methods Cell. Biol.*, 43(A):353–365, 1994; Fynan, Webster, Fuller, Haynes, Santoro, Robinson, *Proc. Natl. Acad. Sci. USA* 90(24):11478–11482, 1993); Viral methods (Clapp, *Clin. Perinatol.*, 20(1):155–168, 1993; Lu, Xiao, Clapp, Li, Broxmeyer, *J. Exp. Med.* 178(6):2089–2096, 1993; Eglitis and Anderson, *Biotechniques*, 6(7):608–614, 1988; Eglitis, Kantoff, Kohn, Karson, Moen, Lothrop, Blaese, Anderson, *Avd. Exp. Med. Biol.*, 241:19–27, 1988); and Receptor-mediated methods (Curiel, Agarwal, Wagner, Cotten, *Proc. Natl. Acad. Sci. USA*, 88(19):8850–8854, 1991; Curiel, Wagner, Cotten, Birnstiel, Agarwal, Li, Loechel, Hu, *Hum. Gen. Ther.*, 3(2):147–154, 1992; Wagner et al., *Proc. Natl. Acad. Sci. USA*, 89 (13):6099–6103, 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, *Plant Physiol.*, 87:671–674,) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al., 1985, *Biotechnology*, 3:629; Rogers et al., 1987, *Meth. in Enzymol.*, 153:253–277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, *Mol. Gen. Genet.*, 205:34; Jorgensen et al., 1987, *Mol. Gen. Genet.*, 207:471.

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various proteins or polypeptides. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985, *Mol. Gen. Genet.*, 199:183; Marcotte et al., *Nature*, 335:454, 1988). Application of these systems to different plant species depends on the ability to regenerate the particular species from protoplasts.

EXAMPLE 1

Cloning of 3'UTR from the Maize Lipase Gene

Complete sequences for maize cDNAs or genomic clones were obtained from the EMBL database. Each was examined to determine if complete 3' UTR was identified. The RNA secondary structure of the 3' UTR sequences was analyzed using the MFOLD and PLOTFOLD subroutines of the GCG software package (Genetics Computer Group, Madison, Wis.). The MFOLD subroutine was developed by Zucker, M., *Science*, 244:44–52, 1989. The folding model utilized is a discrete model. There are no continuously varying parameters, instead either a hydrogen bond exists between two complementary bases or it does not. With a discrete model the mathematical tools exist to compute an optimal folding based on free-energy minimization. The program will find a number of alternate foldings within an energy increment or percentage of the optimal using the energy rules of Frier, S, Proc Natl Acad Sci, USA, 83:9373–9377, 1986. The optimal and near-optimal secondary structures can be graphically displayed using the PLOTFOLD sub-routine. Of the four output routines available within PLOTFOLD, Mountains, Domes, Circles and Squiggles, the Squiggles output is most easily interpreted for long sequences. Sequences were searched for near-consensus, near-upstream poly(A) positioning sequences.

Sequences were obtained by polymerase chain reaction (PCR) of genomic maize DNA. 30 base pair primers were designed from the published sequences which introduced an SstI restriction endonuclease site at the 5' end of the UTR and EcoR1 site and the 3' end. The primers were synthesized of a 394 DNA/RNA Synthesizer (Applied Biosystems, Foster City, Calif.). Amplification reactions were completed with the Expand™ Long Template PCR System (Boehringer Mannheim, Indianapolis, Ind.). Genomic DNA from four inbred lines was used in independent reactions as template. The DNA was extracted from young leaf tissue using standard CTAB procedures (Saghai-Maroof, et al.,. Proc Natl Acad Sci USA 81: 8014–8018, 1984). Probe DNA was prepared using Ready To Go DNA Labelling Beads™ (Pharmacia Biotech, Piscataway, N.J.). Amplifications were cycled in microtiter plates on a Programmable Thermal Controller-10O™ (MJ Research Inc., Water-town, NLA,) with a 56'C. annealling temperature. Amplification products we separated and visualized by 1.2% agarose gel electrophoresis. Resulting amplification products were excised from the agarose and the DNA was purified using QLAEX II Gel Extraction System (Qiagen, Hilden, Germany). The products were ligated into pCR2.1 using the Original TA Cloning Kit (Invitogen Corporation, San Diego, Calif.). Recombinant plasmids were selected on Luria agar (Gibco, Bethesda, Md.) containing 75 mg/liter ampicillin (Sigma, St Louis, Mo.) and 40 ul/plate of a 40 mg/ml stock of X-gal (Boehringer Mannheim, Indianapolis, Ind.). Plasmid DNAs were purified using Wizard™ plus Miniprep DNA Purification System (Promega, Madison, Wis.). DNAs were analyzed and subcloned with restriction endonucleases and T, DNA ligase from Bethesda Research Laboratories (Bethesda, Md.). 3' UTRs were subcloned on SsfIiEcoRJ fragments and final constructs were transformed into DH5α Subcloning Efficiency Competent Cells (Bethesda Research Laboratory, Bethesda, Md.). Sequences of 3' UTRs were verified using Dye Terminator Cycle Sequencing Ready Reaction Kit (Perkin Elmer, Foster City, Calif.) and 373A DNA Sequencer (Applied Biosystems, Foster City, Calif.) and are shown in SEQ ID Nos: 1 and 2.

EXAMPLE 2

Plant Transformation

A. Initiation, Establishment and Maintenance of Embryogenic Maize Suspension Cultures Greenhouse-grown plants of two maize inbred lines, Hi-II A and Hi-II B, are crossed and ears are harvested 10 to 12 days post-pollination. Immature zygotic embryos are aseptically excised and cultured on N6 based medium (Chu et al, 1975, Proc. Symp. Plant Tissue Culture, Peking Press, p43–56) plus AgNO3 (10 mg/L) plus 25 mM L-proline. To initiate suspension cultures, approximately 3 mL packed cell volume (pcv) of healthy 'Type II' callus originating from a single embryo is added to approximately 27 mL of H9CP+ liquid medium. H9CP+ is liquid MS medium (Murashige and Skoog, Physiol. Plant. 15: 473–497,1962) plus 2 mg/L 2,4-D, 2 mg/L NAA, 100 mg/L myo-inositol, 0.69 g/L L-proline, 200 mg/L casein hydrolysate, 30 mg/L sucrose and 5% coconut water (added at subculture) adjusted to pH 6 prior to autoclaving at 121° C. Cultures are maintained in 125 ml Erlemneyer flasks in the dark at 28° C. on a 125 rpm shaker. Cultures typically become established 2 to 3 months after initiation, and are maintained by subculture every 3.5 days. For subculture, 3 ml pcv of cells is measured in a 10 ml wide bore pipet. The measured cells plus 7 ml of old medium is pipetted into 20 ml of fresh medium. Cultures are converted to "large-scale" 500 mL Erlenmeyer flasks by adding 12 mL pcv of cells and 28 mL of old medium to 80 mL of H9CP+ liquid medium using a 50 mL pipet.

B) Preparation of Silicon carbide Whiskers for use in Transformation Experiments:

Autoclavable 50-mL centrifuge tubes (Nalgene) are labeled and weighed. Approximately 500 mg of dry silicon carbide whiskers are added to each tube in a fume hood. An N100 particulate respirator, gloves and a lab coat are worn during this procedure. The caps are screwed back on then re-weighed to determine the whisker weight. Tubes are placed in autoclave pouches, and autoclaved for approximately 30 minutes on a gravity cycle (132° C.). Once cooled, tubes remain in the autoclave pouches until used. For transformation experiments, a 5% w/v whisker suspension is made by adding an appropriate amount of an osmotic culture medium per tube of sterile whiskers. The osmotic medium is liquid N6 medium plus 45 g/L D-sorbitol, 45 g/L D-mannitol, and 30 g/L sucrose, adjusted to pH 6.0 before autoclaving. The whisker suspension is vortexed for 1 minute immediately prior to use.

C) Preparation of Maize Suspension Cultures for use in Transformation Experiments.

Approximately 16 to 24 hours prior to transformation, three flasks, each containing 12 mL pcv of maize suspension cultures plus 40 mL of old medium, are subcultured into 80 ml of liquid N6 medium. On the day of the experiment, all N6 media from each of the 3 flasks prepared the day before is drawn off, and add 72 mL sterile osmotic medium to each flask. The flasks are placed back on a shaker in the dark for 30–35 minutes. After that time period, the contents from all three flasks are pooled into one 250 mL centrifuge bottle. After the cells have settled to the bottom of the tube, all but approx. 14 ml of liquid is drawn off and aseptically added to a 1 L "recovery" flask.

D. WHISKERS™-Mediated Transformation:

The 5% w/v whisker suspension is prepared and vortexed as outlined in part B. Using a 10-mL wide bore pipette, 8100 μl is added to each bottle of cells. 170 μg of plasmid DNA is added to the bottle. The lid is tightly closed, then wrapped with Parafilm, and gently swirled to mix the contents. The bottle is placed in a modified Red Devil™ 5400 commercial paint mixer that has been adapted to hold a 250-mL centrifuge bottle, and agitated for 10 seconds. After agitation, the contents the bottle are transferred to the recovery flask, and an additional 125–130 mL of liquid N6 medium is added to reduce the osmoticum. The recovery flask with cells is placed on a 125-rpm shaker in the dark for a 2 hour recovery.

E. Plating of Whisker-treated Suspension Cells, Selection and Recovery of Stable Transformants:

A sterilized glass cell collector unit is connected to a vacuum, and a sterile 5.5 cm Whatman #4 filter paper is placed on the unit. Two ml of cell suspension is pipetted into the unit, with the vacuum drawing through the liquid, leaving the cells on the filter paper. One flask yields approx. 187 filters of cells. Each filter paper is placed on a 60×20 mm plate of N6 solid medium. Plates are wrapped with 3M micropore tape and placed in the dark for 1 week at 28° C. After 1 week, the filter papers are transferred to 60×20 mm plates containing solid N6 medium+4.5 nM Pursuit® DG (BASF) and re-wrapped. At 2 weeks post-experiment, the tissue from one filtered plate is embedded onto one 100×15 mm plate of N6 medium+4.5 nM Pursuit® DG using 3 mL melted GN6 Agarose medium (liquid N6 medium solidified with 6.5 g SeaPlaque™ agarose per liter containing 4.5 nM Pursuit® DG). Plates are wrapped with either Parafilm or Nescofilm and incubated in the dark at 28° C. Pursuit®-resistant transformants are recovered approximately 3 to 8 weeks post-embedding. They appear as light yellow sectors proliferating against a background of dark yellow to brown growth-inhibited tissue. The growing tissue is placed on fresh selection medium. Transgenic cultures are established after 1 to 2 additional subcultures.

F) Regeneration:

Regeneration is initiated by transferring callus tissue to culture dishes containing a cytokinin-based induction medium, which consists of Murashige and Skoog salts, hereinafter MS salts, and vitamins (Murashige and Skoog, (1962) *Physiol. Plant.* 15: 473–497) 30 g/L sucrose, 100 mg/L myo-inositol, 30 g/L mannitol, 5 mg/L 6-benzylaminopurine, hereinafter BAP, 0.025 mg/L 2,4-D, 4.5 nM Pursuit® DG, and 2.5 g/L GELRITE™ at pH 5.7. The cultures are placed in low light (125 ft-candles) for one week followed by one week in high light (325 ft-candles). Following a two-week induction period, tissue is non-selectively transferred to hormone-free regeneration medium, which is identical to the induction medium except that it lacks 2,4-D and BAP, and is kept in high light. Small (1.5–3 cm) plantlets are removed and placed in 150×25 mm culture tubes containing SH medium (SH salts and vitamins (Schenk, R. V. and A. C. Hildebrandt. 1972. Medium and techniques for induction and growth of monocotyledonous and dicotyledonous plant cell cultures. Can. J. Bot. 50:199–204), 10 g/L sucrose, 100 mg/L myo-inositol, 5 mL/L FeEDTA, and 2.5 g/L GELRITE, pH 5.8). Plantlets are transferred to 10 cm pots containing approximately 0.1 kg of METRO-MIX™ 360 (The Scotts Co. Marysville, Ohio) in the greenhouse as soon as they exhibit growth and develop a sufficient root system. They are grown with a 16 hour photoperiod supplemented by a combination of high pressure sodium and metal halide lamps, and are watered as needed with a combination of 3 independent Peters Excel fertilizer formulations (Grace-Sierra Horticultural Products Company, Milpitas, Calif.). At the 3–5 leaf stage, plants are transferred to 5-gallon pots containing approximately 4 kg METRO-MIX 360. Primary regenerants (R0 plants) are pollinated after an additional 6–10 weeks in 5 gallon pots, and $R_1$ seed is collected at 40–45 days post-pollination. $R_1$ seed is analyzed to identify kernels having the phenotype of interest. These kernels are then planted in 5-gallon pots to obtain plants, which are pollinated to produce $R_2$ seed.

Those skilled in the art will recognize or be able to ascertain, using no more than routine experimentation, many equivalents of the specific embodiments of the invention described herein. Such equivalents are intended to be encompassed by the following claims.

We claim:

1. An isolated DNA molecule consisting of SEQ ID NO: 1.

2. A recombinant expression cassette for effecting expression of a foreign gene in a transformed plant comprising the following operably linked vector elements: a promoter operable in plants, an untranslated leader sequence, a foreign coding sequence of interest, and the 3' untranslated region (3'UTR) comprising the DNA molecule of claim 1.

3. A plant transformed with the expression cassette of claim 2.

4. The plant of claim 3 that is a corn plant.

* * * * *